US012648841B2

(12) United States Patent
Alimi

(10) Patent No.: US 12,648,841 B2
(45) Date of Patent: Jun. 9, 2026

(54) PERCUTANEOUS BYPASS METHOD FOR IMPLANTING A BYPASS GRAFT

(71) Applicants: UNIVERSITÉ D'AIX MARSEILLE, Marseilles (FR); ASSISTANCE PUBLIQUE—HÔPITAUX DE MARSEILLE, Marseilles (FR); Université Gustave Eiffel, Champs-sur-Marne (FR)

(72) Inventor: Yves Alimi, Marseilles (FR)

(73) Assignees: UNIVERSITE D'AIX MARSEILLE, Marseilles (FR); ASSISTANCE PUBLIQUE—HÔPITAUX DE MARSEILLE, Marseilles (FR); UNIVERSITÉ GUSTAVE EIFFEL, Champs-sur-Marne (FR)

( * ) Notice: Subject to any disclaimer, the term of this patent is extended or adjusted under 35 U.S.C. 154(b) by 687 days.

(21) Appl. No.: 18/247,969

(22) PCT Filed: Oct. 6, 2020

(86) PCT No.: PCT/IB2020/000796
§ 371 (c)(1),
(2) Date: Apr. 5, 2023

(87) PCT Pub. No.: WO2022/074412
PCT Pub. Date: Apr. 14, 2022

(65) Prior Publication Data
US 2023/0372078 A1      Nov. 23, 2023

(51) Int. Cl.
*A61F 2/07* (2013.01)
*A61F 2/06* (2013.01)
*A61F 2/962* (2013.01)

(52) U.S. Cl.
CPC ................ *A61F 2/07* (2013.01); *A61F 2/064* (2013.01); *A61F 2/962* (2013.01); *A61F 2002/9623* (2020.05)

(58) Field of Classification Search
CPC .. A61F 2/95; A61F 2/958; A61F 2/954; A61F 2/962; A61B 17/08
See application file for complete search history.

(56) References Cited

U.S. PATENT DOCUMENTS 5,669,924 A * 9/1997 Shaknovich ............ A61F 2/958
606/198
2008/0161901 A1* 7/2008 Heuser .............. A61M 25/0905
623/1.11

(Continued)

OTHER PUBLICATIONS

M. van de Weijer et al; "Morbidity of femoropopliteal bypass sergery"; Seminars in Vascular Surgery, pp. 112-121; 2015 (10 pages).

(Continued)

*Primary Examiner* — Yashita Sharma
(74) *Attorney, Agent, or Firm* — Osha Bergman Watanabe & Burton LLP

(57) ABSTRACT

A percutaneous bypass method for implanting a bypass graft between two vessels is described. The bypass graft comprises a first part and a second part, each having a tubular shape and comprising respective lumens. The method comprises the step of inserting a second sheath, from the outside to the inside of a bypass portion of the first part, through a puncture therein, and retracting the second sheath so as to deploy and implant a hook portion of the second part into the second vessel, and deploy a bypass portion of the second part outside the second vessel, from the second vessel to the first part, and within the lumen of the first part.

14 Claims, 5 Drawing Sheets

(56) References Cited

U.S. PATENT DOCUMENTS

| | | |
|---|---|---|
| 2010/0036475 A1 | 2/2010 | Castaneda |
| 2017/0035591 A1* | 2/2017 | De Pablo Peña ......... A61F 2/06 |
| 2018/0098869 A1* | 4/2018 | Reis ........................ A61F 2/954 |

OTHER PUBLICATIONS

R. J. Exton et al.; "Major Groin Complications Following the Use of Synthetic Grafts"; European Journal Vascular Endovascular Surgery, vol. 34, pp. 188-190; 2007 (3 pages).

K. W. H. Chui et al.; "Review of Direct Anatomical Open Surgical Management of Atherosclerotic Aorto-Iliac Occlusive Disease"; European Journal Vascular Endovascular Surgery, vol. 39, pp. 460-471; 2010 (12 pages).

International Search Report issued in corresponding International Application No. PCT/IB2020/000796, mailed on Jun. 15, 2021 (5 pages).

Written Opinion issued in corresponding International Application No. PCT/IB2020/000796, mailed on Jun. 15, 2021 (8 pages).

* cited by examiner

PERCUTANEOUS BYPASS METHOD FOR IMPLANTING A BYPASS GRAFT

TECHNICAL FIELD

The present disclosure concerns, but is not limited to, a percutaneous bypass method for implanting a bypass graft in order to fluidly connect two vessels. The present disclosure also concerns a surgical kit for implanting such a bypass graft.

TECHNICAL BACKGROUND

Atherosclerosis is a disease in which the inside of an artery narrows due to the buildup of plaque. Plaque rupture may cause artery lumen occlusion within seconds to minutes, leading to potential permanent debility and sometimes sudden death. One manifestation of atherosclerosis is peripheral vascular disease (PVD), i.e. abnormal narrowing of arteries other than those that supply the heart. PVD affects millions of patients worldwide and is a significant cause of major disability, the most common being intermittent claudication. More severe forms may be related with critical ischemia, with e.g., foot or leg ulcer and gangrene, and may lead to limb amputation.

Conventional surgical treatment of PVD consists in implanting a bypass graft that connects a proximal segment of a blocked blood vessel, e.g., pertaining to the femoral artery, with a site distal to the occlusion, e.g., pertaining to the popliteal artery. Both vessels need to be isolated and clamped in order to stop the blood flow while the bypass graft is being attached to both arteries, e.g., by stitching. This open surgical procedure, in the case of femoropopliteal bypasses, leads to significant hospital stays (7-10 days) together with high incidence of mortality (2.3%) and morbidity (36.8% within 30 days) [Refs. 1-2]. Likewise, aorto-femoral bypasses are associated with a morbidity of 16% and a mortality of 4.1%, while ilio-femoral bypasses are associated with a morbidity of 18.9% and a mortality of 2.7% [Ref. 3]. Accordingly, the need for less invasive bypass methods and implant delivery apparatuses remains.

Document US 2010/0036475 A1 describes extraluminal femoropopliteal bypass grafts and methods, and instruments for inserting the same. In particular, a femoropopliteal bypass graft is passed through a first and second apertures formed in a popliteal artery, is then passed through an extraluminal tract, and through a third aperture formed in a femoral artery, so that the proximal end of the graft is disposed within the vascular lumen of the femoral artery and the distal end of the graft is disposed within the vascular lumen of the popliteal artery.

Document US 2018/0098869 A1 describes systems, devices and methods for delivering medical implants such as stent grafts and bypass grafts to bodily vessels, such as blood vessels like peripheral arteries. In particular, the methods relate to the endovascular placement of a stent-graft from an artery, through an adjacent vein, and back to the artery in order to bypass an occlusion in the artery, typically a femoral artery. The methods described therein are typically performed by introducing catheters from the "contralateral" artery into the "ipsilateral" artery, over the branch between the iliacs.

Although they may involve a series of percutaneous steps—thus less invasive than procedural steps of conventional open surgery—the methods described in both of these documents also show shortcomings, e.g., by being constrained to specific target locations, by invading an adjacent vein, and/or by inherently forbidding the use of voluminous prostheses.

GENERAL PRESENTATION

In what follows, the term "comprise" is synonym of (means the same as) "include" and "contains", is inclusive and open, and does not exclude other non-recited elements. Moreover, in the present disclosure, when referring to a numerical value, the terms "about" and "substantially" are synonyms of (mean the same as) a range comprised between 80% and 120%, preferably between 90% and 110%, of the numerical value.

The present disclosure relates to a percutaneous bypass method for implanting a bypass graft between a first vessel and a second vessel in order to fluidly connect said first and second vessels.

In the present disclosure, the term "percutaneous", refers to a step (or series of steps) of a surgical procedure that is (are) performed through the skin, wherein access to vessels, inner organs or other tissue is done via puncture of the skin, as opposed to a procedure performed through conventional open surgery where vessels, inner organs or other tissue are exposed, typically, with the use of a scalpel.

In the present disclosure, by "vessel", it is meant a tubular structure having a lumen, pertaining to the body of a human or animal. This general definition encompasses different types of vessels of a patient, such as vascular vessels or blood vessels, e.g., arteries, veins, arterioles, capillaries. The vessels that are fluidly connected by the method may also be avascular and pertain to the urethra, trachea, branchi, esophagus, biliary tract, gastrointestinal tract.

In the present disclosure, by "fluidly connecting two vessels", it is meant connecting the lumens of two vessels so as to form a common lumen in which a fluid may circulate. By "bypass" or "anastomosis", it is meant a fluidic connection between two vessels, e.g., blood vessels, that are diverging or branching.

The first and second vessels may be part of a vasculature of a patient, and may both be part of a same local vascular network of a patient's body. Alternatively, they may be part of different vascular networks of a patient's body which are either close or remote. The method according to the present disclosure may be suitable for a wide variety of therapeutic uses involving fluidly connecting two vessels of a patient.

Such therapeutic uses may include vascular bypass, such as surgical anastomosis, e.g., side-to-end anastomosis of blood vessels. One objective of a vascular bypass is to redirect blood flow from one area of the patient's body to another by connecting or reconnecting blood vessels. Often, this is done in order to bypass around a diseased area of a patient's body, from an area of normal blood flow to another area of relatively normal blood flow. The diseased area may for example undergo inadequate blood flow (ischemia) caused by an occlusion or blockage affecting one or more vessels of the diseased area. In turn, the occlusion or blockage may be due to the presence in said vessels of one or more clots or plaque. Hence, the method according to the present disclosure may be used to bypass one or more occlusions or blockages present in a network of vessels of a patient's body.

However, the percutaneous bypass method according to the present disclosure may also be used for other purposes, such as providing a vascular access in hemodialysis of a patient.

The method of the present disclosure aims to provide a simple, flexible, non-invasive implantation technique of a bypass graft.

According to a first aspect of the present disclosure, this objective is achieved by a percutaneous bypass method for implanting a bypass graft between a first vessel and a second vessel in order to fluidly connect said first and second vessels, the bypass graft comprising a first part and a second part, each having a tubular shape and comprising respective lumens that are fluidly connected to form a common lumen when the bypass graft is implanted, wherein the method comprises the following steps:

forming a first aperture in a wall of the first vessel;
    partly introducing a first sheath through the first aperture and retracting the first sheath so as to:
        deploy and implant a hook portion of the first part into the first vessel;
        deploy a bypass portion of the first part outside the first vessel;
    forming a puncture in the bypass portion of the first part;
    passing a guide through the puncture and through the lumen of the first part, towards the second vessel;
    forming a second aperture in a wall of the second vessel;
    inserting a second sheath, from the outside to the inside of the bypass portion of the first part, through the puncture and through the lumen of the first part;
    partly introducing the second sheath through the second aperture and retracting the second sheath so as to:
        deploy and implant a hook portion of the second part into the second vessel;
        deploy a bypass portion of the second part outside the second vessel, from the second vessel to the first part, and within the lumen of the first part.

In the present disclosure, by "hook portion", it is meant a portion that is configured to be implanted in a vessel, and not necessarily a portion having the shape of a hook or any other specific shape. Hence, a hook portion constitutes an "anchoring" point in the corresponding vessel wherein the hook portion is configured to be implanted. Further, by the expression "when the bypass graft is implanted", which refers to the bypass graft that is implanted by the percutaneous bypass method according to the first aspect, it is meant that both the first part and the second part of the bypass graft are implanted, i.e., the hook portions of the first and second parts are implanted into the first and second vessels, respectively, and the bypass portions of the first and second parts are deployed. When the bypass graft is implanted, the lumens of both first and second parts are fluidly connected to form a common lumen. Through the common lumen, a fluid, e.g., blood, may be able to circulate.

Hence, the method according to the first aspect allows implanting a bypass graft between two vessels by performing a series of percutaneous steps. The step of forming the puncture in the bypass portion of the first part occurs without trauma for the patient, i.e., in a non-invasive manner. At the same time, the step of forming the puncture allows inserting the second part therethrough, thereby providing improved flexibility to the method. Indeed, as compared to methods wherein a graft formed of one single part is used during implantation, the bypass graft comprises at least two parts in the present disclosure, which get linked to each other and fluidly connected only during implantation, i.e., at the end of the series of steps, when the bypass portion of the second part is deployed within the lumen of the first part. Therefore, the deployment and implantation of the second part is not hindered by the presence of a hypothetical contiguous first part which would for example be contained in the same sheath, and vice versa. The second part may thus be "directly" implanted in the second vessel thanks to the non-invasive platform provided by the bypass portion of the first part, and is not restricted to a large extent by the features specific to the first part, e.g., in terms of dimensions. Likewise, the first part may be easily implanted into the first vessel, in an independent manner, without intermediate steps that would be required by the co-presence of a hypothetical second part of the bypass graft. Hence, the method offers improved simplicity and flexibility during implantation.

The bypass portion of the first part is deployed outside the first and second vessels, for example into perivascular tissues located between the first and second vessels, and provides a convenient extraluminal platform for performing further steps involving the second part of the bypass graft. As such, the method thus stands in contrast with exclusively intraluminal approaches as described, for example, in patent document US 2018/0098869 A.

The bypass portion of the second part is deployed within the lumen of the first part, which leads to the overlapping of the first part and the second part. Hence, simply by retracting the second sheath, an overlap is created, thereby creating a link between the first and second part, and fluidly connecting the first part and the second part.

The above-mentioned characteristics of the method are particularly useful during a surgical intervention, by facilitating the implantation of the bypass graft, and/or by reducing the invasiveness of surgery. For example, the flexibility stemming from the fact that the first and second parts are separate at the beginning of the method facilitates their incorporation into the first and second sheaths, respectively, as well as their positioning, deployment, and implantation within a vessel. The method according to the first aspect of the present disclosure thus aims at improving conventional anastomosis techniques, by providing, among other advantages, a less invasive surgical approach. The inventors have shown that, compared to classic surgical anastomosis, the method according to one or more embodiments of the present disclosure offers advantages, such as, for example, a reduction in skin incision, a reduction in the vessel dissection zone, the avoidance of the use of arterial clamps for interrupting the blood flow, the avoidance of a suture by a vascular thread and/or the avoidance of the placement of a drain. The simplicity of the method provides for reduction in the duration of anastomosis, thereby decreasing ischemia of the organs located in between the first and second vessels, in between which the bypass graft is configured to be implanted. Very advantageously, such positive effects stemming from the series of steps of the method according to the first aspect are accompanied by a substantial decrease in complication rates and shortening of the hospital stays, which may for example be divided by two as compared to conventional open-surgery approaches. The method according to the present disclosure thus represents a further step towards ambulatory surgery.

According to one or more embodiments, the steps of forming the apertures in the walls of the first and second vessels may be performed by using a penetration tool. Examples of penetration tools may include a trocar, a stylet, a needle, a perforating nose, a catheter, a sheath, a probe, a lasso, and combinations thereof. For example, the penetration tool may be a perforating nose having a gradually tapered, conical end for perforating and forming apertures in vessels' walls. Additionally or alternatively, a trocar or needle may be used to perforate a vessel's wall and form an aperture, said trocar or needle containing a hollow cavity through which a guide is passed. The guide is left in place in the vessel while the trocar or needle is withdrawn, and a conical nose is placed on the guide thereafter. The conical nose allows enlarging the aperture. Forming the apertures in the vessels' walls may be performed under control, e.g., under duplex scanning control and/or X-ray control and/or fluoroscopic imaging, at a desired distance of an occlusion or blockage. Duplex scanning control and fluoroscopic imaging may involve the use of duplex scanning markers and fluoroscopic markers, respectively.

According to the present disclosure, deploying the hook portions and bypass portions of each one of the first or second part comprised in the bypass graft is carried out by retracting sheaths, i.e., the retractable first and second sheaths. The first sheath is adapted to contain the first part and is retractable over the first part so as to allow the deployment of the hook and bypass portions of the first part. Likewise, the second sheath is adapted to contain the second part and is retractable over the second part so as to allow the deployment of the hook and bypass portions of the second part. In certain embodiments, the first and second sheaths may have a tubular shape to accommodate the first or second parts of the bypass graft. The first part and the second parts, before implantation of the bypass graft, may be initially constrained within their respective sheaths, so that the steps of retracting the first and second sheaths allow the releasing of the first and second parts from their constraint, respectively, so as to allow their deployment.

In certain embodiments, before being used in the method, each one of the first and second sheaths may come as an outer part of a delivery catheter apparatus comprising an inner shaft, around which the retractable outer sheath is positioned. The delivery catheter apparatuses may be provided with latch mechanisms and other structural features to facilitate outer sheath retraction, as well as with other structural features to prevent undesired compression or shortening of the first and second parts with minimal loss of flexibility. The outer sheath may for example be coupled to at least one latch configured to resist retraction of the sheath. Retracting the outer sheath of the catheter apparatus may comprise tensioning one or more cables of the delivery catheter apparatus over a threshold force, thereby releasing at least one latch so as to allow the at least one latch and the outer sheath to be retracting.

According to one or more embodiments, the hook portion and/or bypass portion of the first part, and the hook portion and/or bypass portion of the second part are radially expandable, and expand radially when retracting, respectively, the first sheath and the second sheath. In certain embodiments, the first and second parts are initially radially constrained within their respective sheaths, and retracting the first or second sheath releases the first or second parts from their radial constraint, respectively, so as to allow their deployment. For example, releasing the hook portion of the first and second part from its radial constraint may allow it to adhere to a vessel wall in which it is configured to be implanted, through its radial force.

In the present disclosure, an axial direction is the direction of the central axis of a tubular part, and a radial direction is a direction perpendicular to said central axis. Similarly, an axial plane is a plane containing the central axis and a radial plane is a plane perpendicular to the central axis. The adverbs "axially" and "radially" refer to the axial and radial direction, respectively. In certain embodiments, at least one of the first part, the second part, or their respective hook and bypass portions may comprise a plurality of branched— contiguously or not—tubular parts which are radially expendable. At least one of the first part, the second part, or their respective hook and bypass portions may for example have substantially a Y-shape, or a T-shape. In these cases, using the expression "radially expendable" when referring to said parts and/or respective portions shall refer to all the radially "expendable" tubular parts that they comprise. For example, if a T is described as radially expendable, it is understood the vertical bar of the T is radially expendable with respect to its own radial direction, and that the horizontal bar of the T is also radially expendable with respect to its own radial direction.

The bypass graft may be configured to be implanted into a specific vessel configuration/network of a patient's body. Accordingly, for a given patient, the features of the bypass graft may be adapted beforehand to the dimensions of the vessel network and/or to any specificity inherent to a given patient's vessel network. In certain embodiments, the dimensions of each one of the first and second part may be adapted to the vessel's dimensions in between which the bypass graft's part is configured to be implanted. For example, the outer diameter the hook portion of the first or second part may be comprised between 1 mm and 50 mm, in particular between 2 mm and 45 mm.

In certain embodiments, at least one of the first part, the second part, or their respective hook and bypass portions may comprise, or consist of, a vascular prosthesis having substantially a straight shape, substantially a Y-shape, or substantially a T-shape, such as for example the vascular protheses described in the international patent application PCT/EP2020/077691. In certain embodiments, combinations of shapes may be envisaged. For example, the first part may have a straight shape, and the second part may have a T-shape, and vice versa, or the first and second parts may both have a straight shape, or may both have a T-shape.

In a T-shaped part or portion of the bypass graft, the horizontal bar of the T is configured to be implanted into the vessel, and the vertical bar is configured to be deployed, partially or totally, outside the vessel. When the first and second vessels are blood vessels, one of the advantages of using a T-shaped part or portion will be that collateral vessels will remain irrigated by blood when the bypass graft is implanted, due to the presence of a free end of the horizontal bar of the T, downstream to the flow of blood circulating in the vessel. This will be particularly important when ischemia of downstream tissues needs to be avoided or mitigated. Such need may not be as important when using a straight-shaped part or portion of the bypass graft. One of the advantages, among others, of using a straight-shaped part as compared to a T-shaped part, may consist in minimizing the space it occupies in the sheath that contains it.

In certain embodiments, the first and second part comprise at least one stent. In certain embodiments, the at least one stent is radially expendable. In the present disclosure, by "stent", it is meant a tubular frame, for example a frame comprising struts. Such a tubular frame is not necessarily closed circumferentially. In certain embodiments, the frame of the at least one stent comprises stent struts, which may be made of a mesh material, e.g., wire mesh. The mesh material may for example include strands of a shape-memory metal braided together with a polymer such as e-PTFE. In certain embodiments, the at least one stent comprises a self-expandable material, which may for example be a thermoelastic material, a shape memory metal or alloy, for example a superelastic alloy (e.g., Nitinol®), or combinations thereof.

The at least one stent comprised in the first and/or second part may be covered and embedded in a covering layer or graft also comprised in the bypass graft. According to one or more embodiments, the bypass graft comprises at least one covering layer or graft, i.e., a fabric having substantially a circular cross-sectional configuration and running along the bypass graft, either partly or totally along the surface thereof. For example, fixation elements at the ends of the first and second parts, may be positioned such that they extent beyond the ends of the graft layer. The at least one stent may be attached to the covering layer or graft, e.g., by adhesive or by suturing. In certain embodiments, one or more stents are not attached to the graft. According to one or more embodiments, the graft may comprise a material which is waterproof and blood tight. Such a material may for example be selected in the group comprising polytetrafluoroethylene (PTFE), a woven or knitted polyester (e.g., Dacron®), polyethylene, polyurethane, silicone, and combinations thereof. The graft may also comprise an inner layer that includes bioactive material having given in vivo properties.

In certain embodiments, the bypass portion of the second part is radially expendable, and retracting the second sheath allows said bypass portion to be released from its radial constraint. The bypass portion of the second part may for example comprise a radially expendable stent positioned at a free end thereof and configured to be deployed within the lumen of the first part. Likewise, the bypass portion of the first part may also comprise a radially expendable stent at a free end thereof. The junction between the free end of the bypass portion of the first part and the free end of the bypass portion of the second part may be carried out by the successive releasing of said radially expendable stents each comprised in their respective bypass portion, and present at the free end of the respective bypass portion. When released, both stents may overlap partially or totally, thereby "locking" the overlap between the first and second parts when the bypass graft is implanted.

According to one or more embodiments, the bypass portion of the first part comprises a region including a flexible material configured to maintain the puncture hermetic when inserting the second sheath therethrough. The region may for example surround the location of the bypass portion of the first part where the puncture is formed. In this way, the second sheath may slide smoothly through the lumen of the first part. Alternatively or additionally, the flexible material may be configured to hermetically seal the puncture when the bypass graft is implanted. In the present disclosure, by "hermetically sealed", it is meant "leading to substantially no leak", referring to a fluid that may circulate through the bypass graft. For example, no substantial blood leakage occurs when the bypass graft is implanted between two blood vessels. According to one or more embodiments, the flexible material is made of substantially the same material as the rest of the bypass portion of the first part, and has a thickness superior to the thickness of the rest of the bypass portion of the first part, for example twice said thickness, for example thrice said thickness. According to one or more embodiments, the flexible material is selected in the groups comprising self-healing materials. According to one or more embodiments, the flexile material may comprise rubber. In certain embodiments, the bypass portion of the first part comprises at least one marker, e.g., a fluoroscopic marker and/or a duplex scanning marker so that the step of forming the puncture may be closely monitored. For example, when the bypass portion of the first part comprises the region including the above-mentioned flexible material, the marker may be contained in said region.

In certain embodiments, an automatic closing device may be used to hermetically seal the puncture formed in the bypass portion of the first part, once the second sheath is fully retracted from the lumen of the first part and once the bypass portion of the second part is fully deployed. The automatic closing device delivers a patch that is able to remain attached to the bypass graft, while hermetically sealing the puncture. Examples of automatic closing devices may for example be selected in the group comprising: MYNXGRIP® vascular closing device, PROSTAR XL® (Abbott Vascular INC), STARCLOSE® (Abbott Vascular Inc), ANGIOSEAL® (Terumo), EXOSEAL® (Cordis).

According to one or more embodiments, the second sheath has an outer diameter comprised between 1 mm (4 Fr) and 10 mm (30 Fr). According to one or more embodiments, the second sheath has an outer diameter of at least 4 mm, corresponding to 12 French (12 Fr). According to one or more embodiments, the outer diameter of the second sheath is at least 4.333 mm (13 Fr), for example at least 4.667 mm (14 Fr), at least 5 mm (15 Fr), at least 5.333 mm (16 Fr), and for example comprised between 4 mm (12 Fr) and 10 mm (30 Fr). The dimensions of the second sheath are adapted to the dimensions of the second part of the bypass graft, which is contained in the second sheath. Very advantageously, thanks to the above-mentioned features characterizing the method according to the first aspect, the method of the present disclosure provides an important margin of freedom to surgeons, in particular in terms of the dimensions of the second sheath, i.e., the sheath containing the second part of the bypass graft. The method according to the first aspect allows using big sheaths, e.g., having an outer diameter of at least 5.333 mmm (16 Fr), thereby allowing the implantation of voluminous parts of the bypass graft, such as for example voluminous vascular prostheses having substantially a T-shape. One of the potential problems occurring when using sheaths which are too small is that the aperture formed in the wall of the vessel, through which the sheath is partly introduced, is also too small, leading to compressing the prosthesis or part of the bypass graft configured to be implanted into and/or deployed outside the vessel. Such compression, which occurs at the level of the aperture, may for example result in a mediocre patency of the bypass graft.

Regarding, for example, the specific configuration of a femoropopliteal bypass, e.g., the first vessel being a popliteal artery and the second vessel a femoral artery, this advantage turns out to be crucial if voluminous sheaths are needed. The extraluminal platform provided by the bypass portion of the first part, that is punctured to insert the second sheath therethrough, from the outside to the inside, allows the surgeons to avoid advancing sheaths by introducing catheters intraluminally from the "contralateral" artery, from the opposite leg of the patient, into the "ipsilateral" artery, i.e., over the branch between the iliacs, thereby avoiding tortuous, narrow ways.

According to one or more embodiments, the percutaneous bypass method is a method for implanting a bypass graft between two blood vessels of a patient, for example between two arteries, between an artery and a vein, or between two veins. According to one or more embodiments, the first and second vessels may comprise or consist of one or more vessels that are selected in the group comprising an aorta, a common carotid artery, a brachio-cephalic trunk, an external carotid artery, an internal carotid artery, a subclavian artery, an axillary artery, a brachial artery, a radial artery, an ulnar artery, a thoracic aorta, an abdominal aorta, a hypogastric artery, an external iliac artery, an internal iliac artery, a superior mesenteric artery, an inferior mesenteric artery, a renal artery, a femoral artery, a popliteal artery, an anterior tibial artery, a dorsalis pedis artery, a posterior tibial artery, a fibular artery, an arch of foot artery, a pulmonary vein, a vena cava, a superior vena cava, an inferior vena cava, an iliac vein, a portal vein, an humeral vein, a radial vein, a cubital vein, a small saphenous vein, a superior mesenteric vein, a jugular vein, an internal jugular vein, a subclavian vein, an axillary vein, a pulmonary artery, a cephalic vein, a basilic vein, a renal vein, a femoral vein, or a great saphenous vein.

In certain embodiments, the method is a method for implanting a femoropopliteal bypass graft. For example, the first vessel is a popliteal artery and/or the second vessel is a femoral artery. According to one or more embodiments, the second vessel is a common femoral artery or a superficial femoral artery. In certain embodiments, the second vessel is a common femoral artery, and the method may for example allow bypassing an important occlusion located in the superficial artery. Within the frame of a vascular bypass, a common femoral will typically necessitate vascular prostheses having bigger dimensions than the ones adapted to a superficial femoral artery. Interestingly, the advantages of the method of the present disclosure described vide supra with reference to the dimensions of the second sheath will facilitate such bypass between a popliteal artery and a common femoral artery, and make it stand out from known methods.

According to one or more embodiments, a blood flow through the first vessel and/or the second vessel is occluded, in order to interrupt blood flow during implantation of the bypass graft. For this purpose, different types of balloon catheters may be used as an occlusive device, such as for example simple or double balloon catheters. In certain embodiments, the way to occlude the first vessel and/or the second vessel is not restricted to the use of balloons, and may for example involve sheaths having conical, gradually tapered, puncturable ends, that may be punctured and re-sealed easily.

According to one or more embodiments, at least one step of the method is performed under duplex scanning (or Doppler sonography) control and/or X-Ray control and/or fluoroscopic imaging. Additionally, at least one step of the method may further be performed under fluoroscopic imaging.

According to a second aspect, the present disclosure concerns a surgical kit for implanting a bypass graft between a first vessel and a second vessel in order to fluidly connect said first and second vessels. The surgical kit according to the second aspect may be used to carry out the percutaneous bypass method according to the first aspect of the present disclosure. The surgical kit according to the second aspect comprises:

a bypass graft with a first part and a second part, each having a tubular shape and comprising respective lumens that are adapted to be fluidly connected to form a common lumen when the bypass graft is implanted; wherein:

the first part comprises a hook portion configured to be deployed and implanted into the first vessel, and a bypass portion configured to be deployed outside the first vessel; and the second part comprises a hook portion configured to be deployed and implanted in the second vessel, and a bypass portion configured to be deployed outside the second vessel and within the lumen of the first part;

and wherein:

the bypass portion of the first part is puncturable;

a first retractable outer sheath adapted to contain the first part and retractable over the first part so as to allow the deployment of the hook portion and bypass portion of the first part;

a second retractable outer sheath adapted to contain the second part and retractable over the second part so as to allow the deployment of the hook portion and bypass portion of the second part.

In certain embodiments, the bypass portion of the first part comprises a region including a flexible material configured to receive a puncture and hermetically accommodate the second retractable outer sheath when said sheath is inserted through the puncture and/or configured to hermetically seal the puncture when the bypass graft is implanted. In certain embodiments, the flexible material is made of substantially the same material as the rest of the bypass portion of the first part, and has a thickness superior to the thickness of the rest of the bypass portion of the first part, for example twice said thickness, for example thrice said thickness. The flexible material may be selected in the groups comprising self-healing materials. In certain embodiments, the bypass portion of the first part comprises at least one marker, e.g., a fluoroscopic marker and/or a duplex scanning marker. For example, when the bypass portion of the first part comprises the region including the above-mentioned flexible material, the at least one marker may be contained in said region.

In certain embodiments, the hook portion and bypass portion of the first part, and the hook portion and bypass portion of the second part are radially expandable.

In certain embodiments, the second sheath has an outer diameter comprised between 1 mm (3 Fr) and 10 mm (30 Fr). In certain embodiments, the second sheath has an outer diameter of at least 4 mm, corresponding to 12 French (12 Fr). According to one or more embodiments, the outer diameter of the second sheath is at least 4.333 mm (13 Fr), for example at least 4.667 mm (14 Fr), at least 5 mm (15 Fr), at least 5.333 mm (16 Fr), and for example comprised between 4 mm (12 Fr) and 10 mm (30 Fr).

All the features of the bypass graft mentioned vide supra with reference to the bypass graft configured to be implanted by the method according to the first aspect may be present in the bypass graft comprised in the surgical kit according to the second aspect of the present disclosure.

In certain embodiments, the surgical kit may further comprise one or more items selected among the group comprising delivery catheters having retractable outer sheaths, sheaths having a penetration tool for penetrating a vessel. Examples of penetration tools may include a trocar, a stylet, a needle, a perforating nose, a catheter, a sheath, a probe, a lasso, and combinations thereof. For example, the penetration tool may be a perforating nose having a gradually tapered, conical end for perforating and forming apertures in vessels' walls. The implantation sheath, e.g., the first and second sheaths, may include additional items that may ease the deployment and implantation of the bypass graft, such as a peel-away sheath, a ripcord, a mechanical clamp, a guide, for example a hydrophilic guide. During an implantation procedure, such a guide may be used to insert a prosthesis within a vessel, and perform a step of positioning said prosthesis in a targeted location of the vessel.

According to one aspect, the present disclosure concerns a method for treating a peripheral vascular disease affecting a patient, comprising the use of the percutaneous bypass method as defined in the first aspect of the present disclosure.

Other features and advantages of the invention will become apparent from the following detailed description, taken in conjunction with the accompanying drawings, which illustrate, by way of example, the principles of the invention.

BRIEF DESCRIPTION OF THE DRAWINGS

In the drawings, like reference signs generally refer to the same or like parts throughout the different views.

The drawings are not necessarily to scale, emphasis instead generally being placed upon illustrating the principles of the invention.

DETAILED DESCRIPTION OF EXAMPLES

Examples of methods and surgical kits will now be described in detail with reference to the accompanying figures. In the following detailed description, numerous specific details are set forth in order to provide a more thorough understanding of the present disclosure. However, it will be apparent to one of ordinary skill in the art that the present disclosure may be practiced without these specific details. In other instances, well-known features have not been described in detail to avoid unnecessarily complicating the description.

The following description provides non-limiting examples of methods and surgical kits according to the first and second aspects, respectively, of the present disclosure. The description further provides non-limiting details concerning potential applications of the method for implanting a bypass graft according to the present disclosure.

Figure 1B:
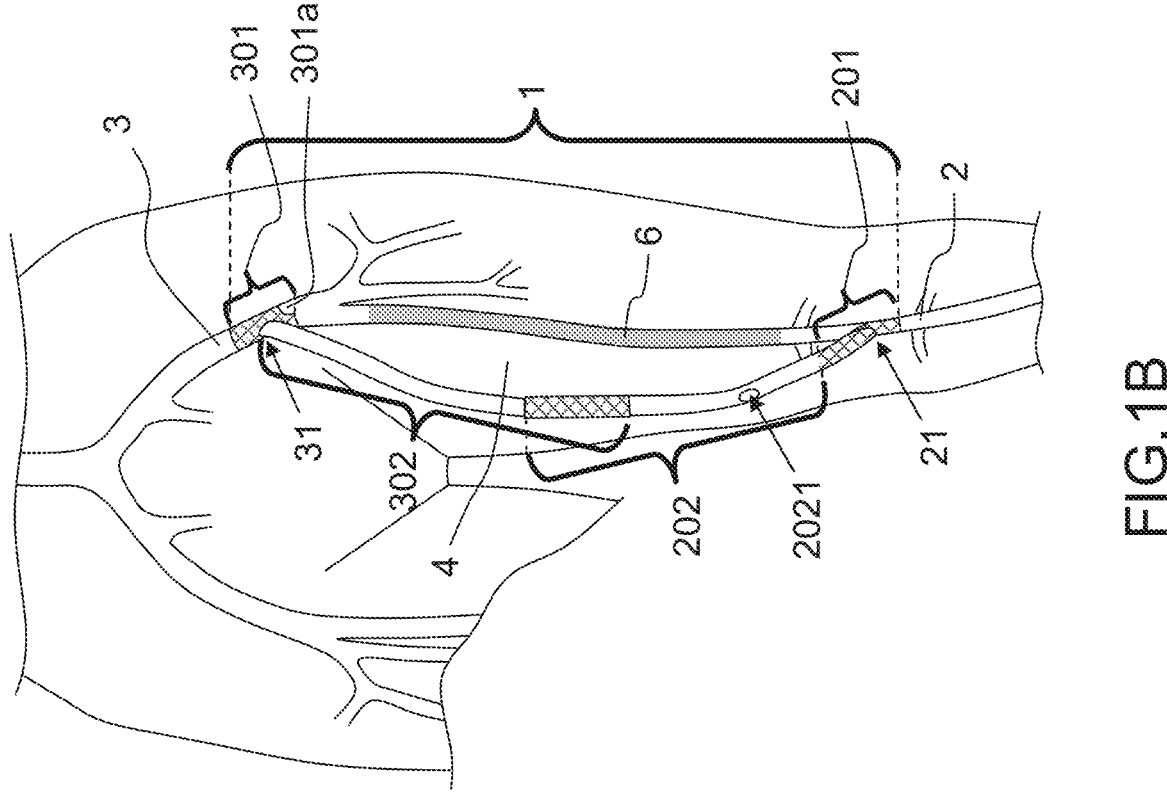
FIG. 1B is a top view of a diagrammatic representation of a similar bypass graft as compared to the one shown in FIG. 1A, and implanted by performing another embodiment of the method according to the first aspect of the present disclosure.
Figure 1A:
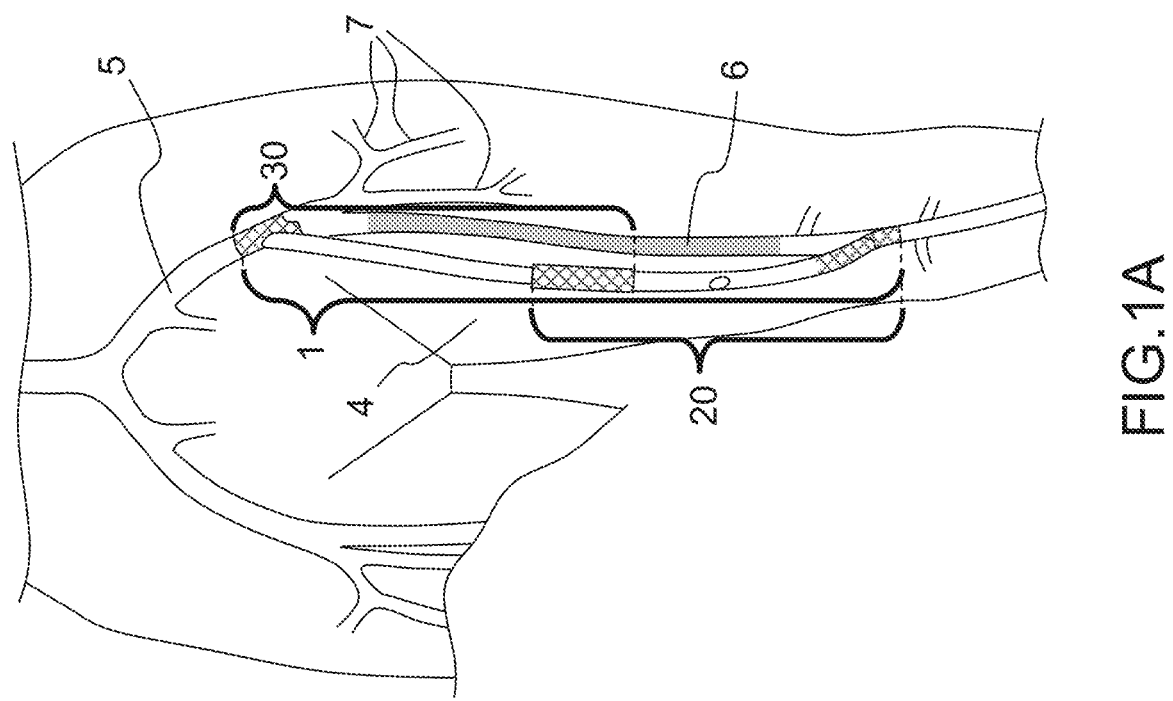
FIG. 1A is a top view of a diagrammatic representation of an example of implanted bypass graft, with reference to one or more embodiments of the method according to the first aspect and with reference to one or more embodiments of the surgical kit according to the second aspect of the present disclosure.
Figure 2:
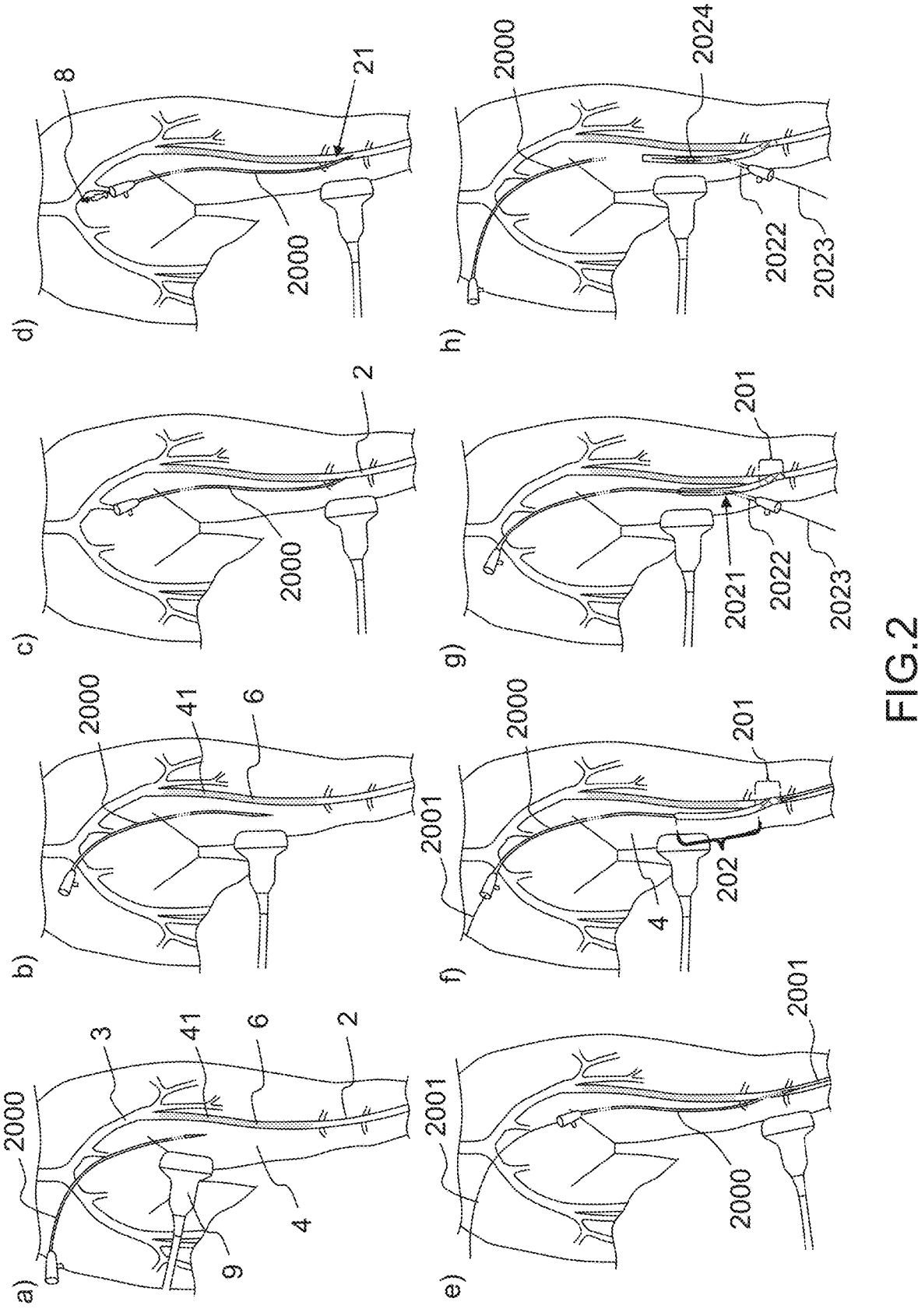
FIG. 2 $a$) to $h$) are top views of diagrammatic representations illustrating different snapshots in time of the method for implanting the bypass graft shown in FIG. 1A.
Figure 3:
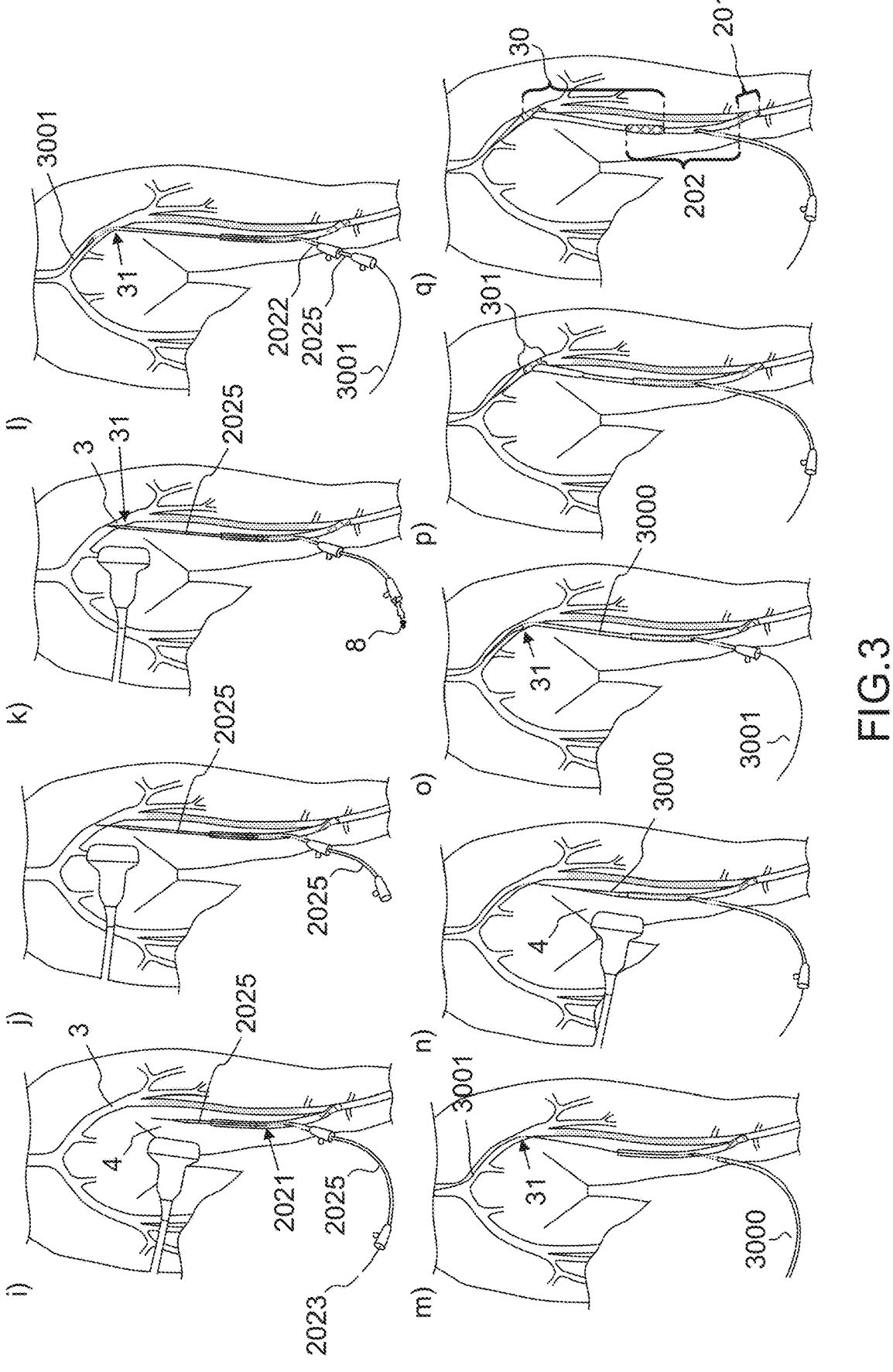
FIG. 3 $i$) to $q$) are top views of diagrammatic representations illustrating different snapshots in time of the method—illustrated in FIG. 2 $a$) to $h$)—for implanting the bypass graft shown in FIG. 1A.
Figure 4:
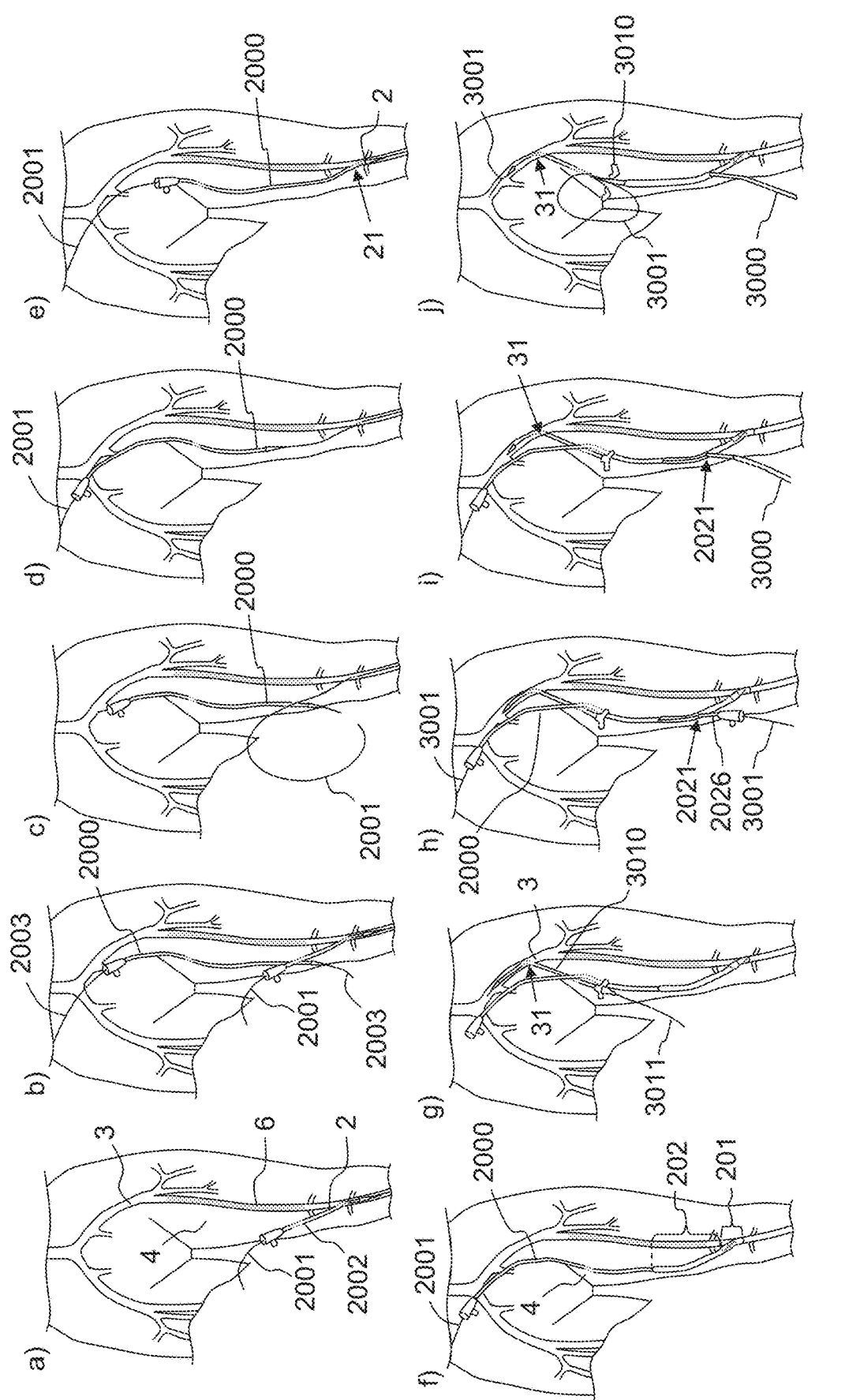
FIG. 4 $a$) to $j$) are top views of diagrammatic representations illustrating different snapshots in time of the method for implanting the bypass graft shown in FIG. 1B.
Figure 5:
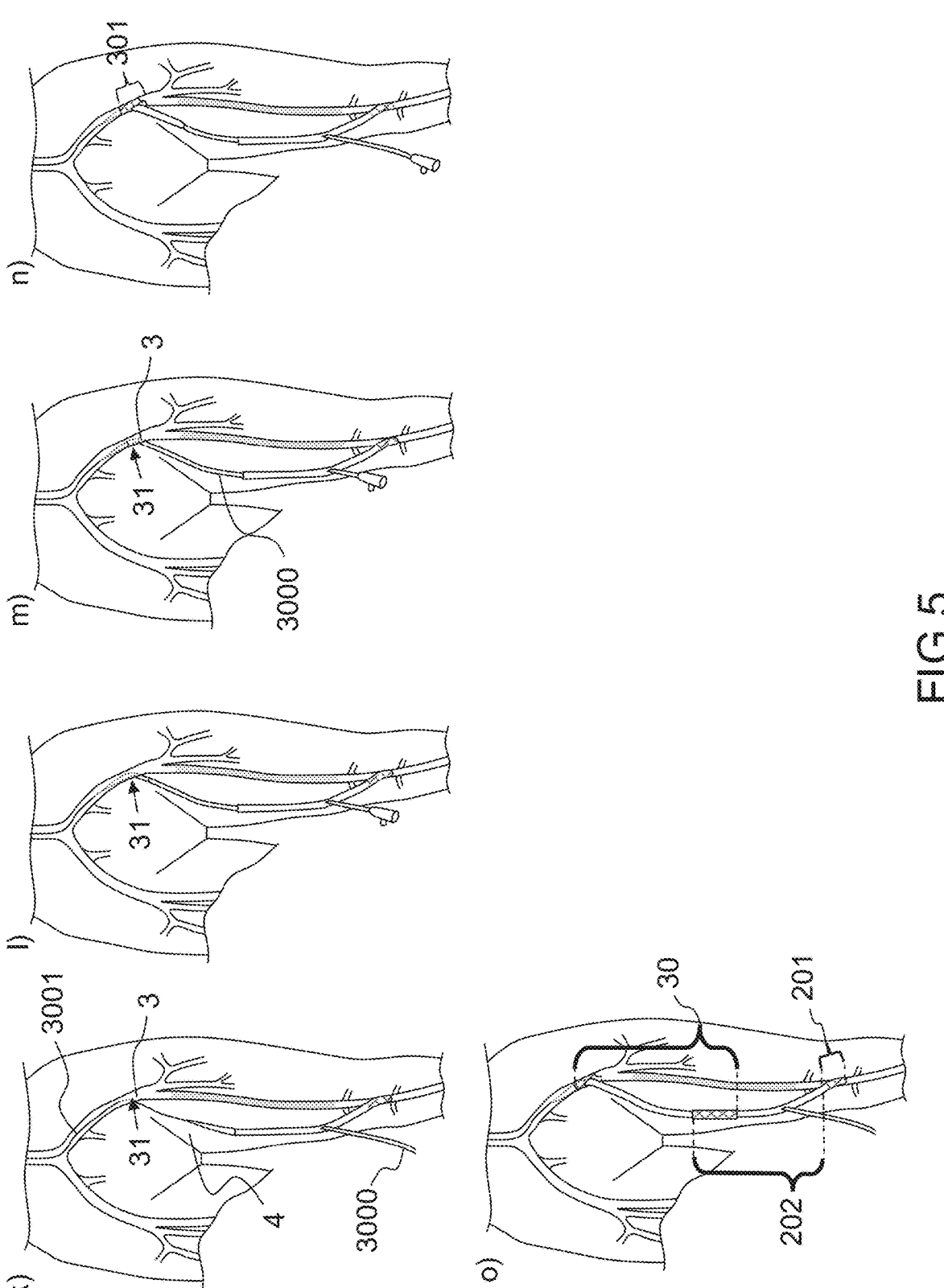
FIG. 5 $k$) to $o$) are top views of diagrammatic representations illustrating different snapshots in time of the method—illustrated in FIG. 4 $a$) to $j$)—for implanting the bypass graft shown in FIG. 1B.

One example of (implanted) bypass graft according to the second aspect of the present disclosure is shown in FIG. 1A. The bypass graft shown in FIG. 1B is similar to the one shown in FIG. 1A, and is implanted by performing another embodiment of the method according to the first aspect. The difference between the two embodiments of the method according to the first aspect is further detailed below with reference to the following FIGS. 2-5. FIGS. 2-3 illustrate different snapshots in time of the method called "deep", while FIGS. 4-5 illustrate different snapshots in time of the method called "superficial". FIG. 1A illustrates the result of the method called "deep", while FIG. 1B illustrates the result of the method called "superficial". In these two examples of methods, the bypass graft which is implanted comprises substantially the same parts, and like reference signs refer to the same parts.

In FIGS. 1A and 1B, the bypass graft is designated by reference number 1 and is in a configuration where it is implanted between a first vessel 2 and a second vessel 3. In these examples, the first vessel 2 is the (left) popliteal artery of the patient and the second vessel is the (left) common femoral artery 3. The bypass graft 1 is thus called a femoropopliteal bypass graft in this example, and is implanted percutaneously through perivascular tissues 4, downstream of the external iliac artery 5, in order to bypass around a diseased area of a patient's body, from an area of normal blood flow to another area of relatively normal blood flow. The diseased area or occlusion is designated by reference 6 and is an occlusion due to plaque in this example.

As shown in FIGS. 1A-1B, the bypass graft 1 comprises a first part 20 and a second part 30, each having a tubular shape and comprising respective lumens that are fluidly connected to form a common lumen when the bypass graft 1 is implanted.

The first part 20 comprises a hook portion 201 configured to be deployed and implanted into the first vessel 2, and a bypass portion 202 configured to be deployed outside the first vessel 2. Likewise, the second part 30 comprises a hook portion 301 configured to be deployed and implanted into the second vessel 3, and a bypass portion 302 configured to be deployed outside the second vessel 3 and within the lumen of the first part 20.

In this example, the first part 20 is a straight-shaped vascular prosthesis implanted in the popliteal artery 2, which extends outside of the vessel, through the aperture 21 formed in the wall of the artery, in the perivascular tissues 4, and towards the second vessel, i.e., the common femoral artery 3. In other examples, the first part may be a T-shaped vascular prosthesis, and the choice between a straight-shaped and a T-shaped may depend on the surgeon and/or on the occlusion 6. As shown in FIG. 1B, the hook portion 201 of the first part 20 comprises a stent which extends over its entire length. In this example, such stent is radially expendable, and expands radially when retracting the sheath containing the first part 20, during implantation.

Further, in this example, the second part 30 is a T-shaped vascular prosthesis implanted in the common femoral artery 3, which extends outside of the vessel, through the aperture 31 formed in the wall of the artery, in the perivascular tissues 4, and towards the first vessel, i.e., the popliteal artery 2. In such T-shaped configuration of the second part 30, the horizontal bar of the T, i.e., the hook portion 301, is implanted in the common artery 3, and the vertical bar of the T, i.e., the bypass portion 302, extends outside the vessel. Due to the presence of a free end of the horizontal bar of the T, downstream of the flow of blood circulating in the vessel 3, collateral vessels 7 remain irrigated by blood (not shown) when the bypass graft 1 is implanted, thereby minimizing or avoiding the risk of ischemia of the downstream tissues being irrigated by said vessels 7. In this example of hook portion 301, said free end further comprises a scallop or circumferential indentation 301$a$, thereby minimizing the space that the T-shaped prosthesis or second part 30 occupies in the sheath that contains it prior to and during implantation. Examples of such T-shaped vascular prostheses mitigating the invasiveness of the surgical procedure are for example described in the international patent application PCT/EP2020/077691.

In this example, as further shown in FIGS. 1A and 1B, the first part 20 and the second part 30 comprise a graft covering layer having substantially a circular cross-sectional configuration and running along the bypass graft and totally along the surface thereof. Such graft comprises a material which is waterproof and blood tight and is selected in the group comprising polytetrafluoroethylene (PTFE), a woven or knitted polyester (e.g., Dacron®), polyethylene, polyurethane, silicone, and combinations thereof.

As shown in FIG. 1A, the first part 20 and the second part 30 partly overlap, thereby creating a junction located substantially at the middle of the bypass graft 1. In this example, as shown in more detail in FIG. 1B, the bypass portion 302 of the second part 30 comprises a stent positioned at a free end of the second part 30, which is deployed within the lumen of the first part 20. The bypass portion 202 of the first part 201 also comprises a stent at a free end thereof. In this example, both stents are radially expendable, and expand radially when retracting the respective sheath that contain them. In this example, both stents overlap "totally", i.e., over their entire length. However, other configurations wherein the overlap is partial may also be envisaged, which still lead to fluidly connecting the first and second parts.

Reference 2021 designates a patch added by an automatic closing device, in order to hermetically seal the puncture formed in the bypass portion 202 of the first part 20, i.e., the puncture through which, during implantation, the sheath containing the second part 30 is inserted. Alternatively, yet in a combinable manner, in one or more embodiments of the method or the surgical kit according to the present disclosure, hermetically sealing the puncture when the bypass graft is implanted is ensured by the presence of a flexible material comprised in a region of the bypass portion 202.

In this example, the bypass portion 202 of the first part 20 comprises a duplex scanning marker and a fluoroscopic marker (not shown) which are positioned in the region of the bypass portion 2021 wherein the puncture is patched. The role of these marker is to offer more control to the surgeon during implantation of the bypass graft, e.g., while performing the puncture in the bypass portion 202.

Described below is a non-limiting example of surgical kit according to the second aspect of the present disclosure. The surgical kit contains the parts of the femoropopliteal bypass graft described above and illustrated in FIGS. 1A-1B, wherein the bypass portion 202 of the first part 20 is configured to be puncturable. The surgical kit further comprises:

a first retractable outer sheath 2000 adapted to contain the first part 20 and retractable over the first part 20 so as to allow the deployment of the hook portion 201 and bypass portion 202 of the first part 20;

a second retractable outer sheath 3000 adapted to contain the second part 30 and retractable over the second part 30 so as to allow the deployment of the hook portion 301 and bypass portion 302 of the second part 30.

The first sheath is for example depicted in FIG. 2c) and designated by reference number 2000. In this specific example of surgical kit, the first sheath 2000 has an outer diameter of 2.667 mm (8 Fr). The second sheath 3000 is for example illustrated in FIG. 2o) and has an outer diameter of 5.333 mm (16 Fr).

In this example, the surgical kit comprises other items such as delivery catheters apparatuses, other sheaths than the first and second sheaths 2000, 3000 sheaths, e.g., sheaths having a penetration tool for penetrating a vessel, and additional items such as peel-away sheaths, ripcords, mechanical clamps, latches, slots, cables, guides, catheters, probes, lassos, balloon catheters, and combinations thereof.

Described below are two different non-limiting examples of methods according to one or more embodiments of the percutaneous bypass method according to the first aspect of the present disclosure, which are illustrated in FIGS. 2-5.

FIGS. 2-3 illustrate different snapshots in time of the method called "deep", while FIGS. 4-5 illustrate different snapshots in time of the method called "superficial".

The choice between the two methods may result from a compromise between the pain inflicted to a patient and the experience of the surgeon performing the steps of the method. The "deep" method creates a deep bypass route between the two vessels, is more difficult to perform than the "superficial" method, but leads to less pain for the patient when the bypass graft is implanted, because the created bypass route is in close contact with the superficial femoral artery axis. Conversely, the "superficial" method is easier to perform, but leads to more pain for the patient when the bypass graft is implanted.

Deep Method:

The result of this method is the percutaneous implantation of bypass graft 1 between a popliteal artery 2 and a common femoral artery 3, as illustrated in FIG. 1A.

The following steps a)-q) described below are also illustrated in the corresponding FIGS. 2a) to 2h) and 3i) to 3q), respectively:

a) Under local anesthesia, introduction of a 8-Fr sheath 2000 having an outer diameter of 2.667 mm in the ipsilateral groin tissue under duplex scanning control, using a duplex scanner 9.

b) After tumescent anesthesia, the long 8-Fr sheath 2000 is gradually pushed deep under the thigh skin, close to the superficial femoral artery 41, under duplex scanning control.

c) The 8-Fr sheath 2000 is then brought into contact with the patent popliteal artery 2.

d) An aperture 21 is then formed in a wall of the popliteal artery 2, under duplex scanning control. Blood 8 is ejected from the sheath 2000.

e) A guidewire 2001 is then placed in the popliteal artery 2 through the 8-Fr sheath 2000, under duplex scanning and X-ray control. The sheath 2000 is partly introduced in through the aperture 21.

f) Retracting the sheath 2000 allows deploying and implanting the hook portion 201, a regular covered self-expanding stent, into the popliteal artery 2, and deploying the bypass portion 202, a 7 mm-diameter PTFE graft distally maintained into the sheath 2000, outside the vessel 2.

g) The guidewire 2001 is removed. A puncture 2021 in bypass portion 202 of the first part 20 is performed under duplex scanning, and a 7-Fr sheath 2022 having an outer diameter of 2.667 mm is introduced with a guidewire 2023.

h) A balloon 2024 placed around the 7-Fr sheath 2022 is inflated, in order to avoid backflow from the popliteal artery 2, and then the proximal 8-Fr sheath 2000 is removed.

i) A long 6-Fr sheath 2025 having an outer diameter of 2 mm is then introduced inside the 7-Fr sheath 2022, j) The 6-Fr sheath 2025 is advanced in the groin tissue 4 and brought into contact with the common femoral artery 3, under duplex scanning control. Then, the guidewire 2003 is removed.

k) An aperture 31 is then formed in a wall of the common femoral artery 3. Blood 8 is ejected from the sheath 2025.

l) A guidewire 3001 is then introduced in the common femoral artery 3 with the tip placed in the aorta, under X-ray control.

m) The 6-Fr sheath 2025 and the 7-Fr sheath 2022 are removed and a 16-Fr sheath 3000, having an outer diameter of 5.333 mm, is introduced on the guidewire 3001 and inserted, from the outside to the inside of the bypass portion 202 of the first part 20, through the puncture 2021 and through the lumen of the first part 20 of the bypass graft 1.

n) The16-Fr sheath 3000 is progressively pushed further through the groin tissue 4.

o) The16-Fr sheath 3000 is then slipped inside the left common femoral artery 3, under X-ray control.

p) Retracting the sheath 3000 allows deploying and implanting the second part 30, i.e., a T-shaped vascular prosthesis, having a hook portion 301, i.e., the horizontal bar of the "T", and a bypass portion 302, i.e., the vertical bar of the "T".

q) Retracting the sheath 3000 allows deploying the bypass portion 302 of the second part 30 within the lumen of the first part 20 and releasing a self-expendable stent at the level of the overlap between the first part 20 and the second part 30, under X-ray control. The 16-Fr sheath 3000 and the guidewire 3001 are then removed from the puncture 2021, which is closed by using an automatic closing device (not shown). The result of the bypass procedure is shown in FIG. 1A.

Superficial Method:

The result of this method is the percutaneous implantation of bypass graft 1 between a popliteal artery 2 and a common femoral artery 3, as illustrated in FIG. 1B.

The following steps a)-p) described below are also illustrated in the corresponding FIGS. 4a) to 4j) and 5k) to 5o), respectively:

a) Under local anesthesia, placement of a guidewire 2001 and a 4-Fr sheath 2002 having an outer diameter of 1.333 mm in the left popliteal artery 2, thereby forming an aperture 21 in a wall of the vessel 2.

b) Under tumescent anesthesia, a long 8-Fr sheath 2000 is placed deep under the thigh skin, from the left femoral puncture site to the left popliteal puncture site, and then exteriorized at the site of the left popliteal puncture site.

c) The guide 2003 is removed from the sheath 2000, thereby allowing to introduce the proximal part of the left popliteal guidewire 2001 inside the sheath 2000 placed under the left thigh skin.

d) The sheath 2000 is then pulled back a few centimeters under the skin.

e) The 8-Fr sheath 2000 is then pushed inside the left popliteal artery 2.

f) Retracting the sheath 2000 allows deploying and implanting the hook portion 201, a regular self-expanding stent, into the popliteal artery 2, and deploying the bypass portion 202, a 7 mm-diameter PTFE graft distally maintained into the sheath 2000, outside the vessel 2.

g) A guidewire 3011 and a 4-Fr peel-away-sheath 3010 having an outer diameter of 1.333 mm are used to form an aperture 31 in a wall of the left common femoral artery 3 and are placed in vessel 3. The guidewire 2001 placed in the 8-Fr sheath 2000 is removed.

h) The guide 3011 is removed. A puncture 2021 in bypass portion 202 of the first part 20 is performed under duplex scanning, and a 4-Fr sheath 2026 having an outer diameter of 1.333 mm is introduced, together with a guidewire 3001. The guidewire 3001 is passed through the puncture 2021 and moved from the 4-Fr sheath 2026 to the 8-Fr sheath 2000, with the possible help of a lasso.

i) The 4-Fr sheath 2026 is then removed and a 16-Fr sheath 3000, having an outer diameter of 5.333 mm, is introduced on the guidewire 3001 and inserted, from the outside to the inside of the bypass portion 202 of the first part 20, through the puncture 2021 and through the lumen of the first part 20 of the bypass graft 1.

j) The proximal 8-Fr sheath 2000, placed under the left thigh skin, is removed. The guidewire 3001 is then placed in the 4-Fr peel-away-sheath 3010, and is then placed inside the left common femoral artery 3. The 4-Fr peel-away-sheath 3010 is then removed.

k) The tip of the guidewire 3001 is placed in the aorta.

l) The 16-Fr sheath 3000 is then progressively pushed further the tissues 4, and inside the left common femoral artery 3.

m) and n) Retracting the sheath 3000 allows deploying and implanting the second part 30, i.e., a T-shaped vascular prosthesis, having a hook portion 301, i.e., the horizontal bar of the "T", and a bypass portion 302, i.e., the vertical bar of the "T".

o) Retracting the sheath 3000 allows deploying the bypass portion 302 of the second part 30 within the lumen of the first part 20 and releasing a self-expendable stent at the level of the overlap between the first part 20 and the second part 30. The 16-Fr sheath 3000 and the guidewire 3001 are then removed from the puncture 2021, which is closed by using an automatic closing device (not shown). The result of the bypass procedure is shown in FIG. 1B.

As mentioned above, these two percutaneous bypass techniques allow avoiding "crossover" femoral manipulation, and using large 16-Fr sheaths which are directly introduced in the diseased limb, in order to deploy a voluminous T-shaped vascular prosthesis in the common femoral artery. Compared to conventional open surgery, within the frame of a femoropopliteal bypass, these methods may provide the following non exhaustive list of advantages:

reduces inguinal incision: 2 to 5 cm (versus 10 cm for surgery);

reduces arterial dissection zone: 1 to 3 cm (versus 5 cm for surgery);

avoids the use of arterial clamps (upstream and downstream the vessel);

avoids suture by a vascular thread;

avoids the placement of a drain;

reduces the duration of anastomosis to 1-4 minutes (versus 15-30 minutes).

Conventional femoropopliteal bypass open surgery is associated with a morbidity of 36.8% and a mortality of 2.3%, mostly related to the inguinal incision, with an average hospital stay of 10.2 days [Refs. 1-2]. The technical benefits of the methods according to the present disclosure allow a significant reduction in the rate of complications and a hospital stay divided by two.

The method and surgical kit according to the present disclosure may also be used to perform aorto-femoral bypasses (associated with a morbidity of 16% and a mortality of 4.1% for open surgery), and ilio-femoral bypasses (associated with a morbidity of 18.9% and a mortality of 2.7% for open surgery) [Ref. 3]. The method and surgical kit according to the present disclosure may also be used, for example, to perform bypasses between an axillary artery and a femoral artery, between a femoral artery and a contralateral femoral artery, or between a primitive carotid and an internal carotid. Other applications may concern dialysis and the implantation of a bypass graft between an artery and a vein.

The embodiments described above are not exhaustive. In particular, it is understood that additional embodiments can be considered on the basis of different combinations of the explicitly described embodiments. Unless otherwise specified in the present disclosure, it will be apparent to the skilled person that all the embodiments described above can be combined together. For example, unless otherwise specified, all features of the embodiments described above, whichever embodiment of the percutaneous bypass method or the surgical kit they refer to, can be combined with or replaced by other features from other embodiments.

The above description is given by way of example, and not limitation. Given the above disclosure, one skilled in the art could devise variations that are within the scope of the invention defined by the appended claims. In particular, the various features of the embodiments or examples disclosed herein can be used alone or in varying combinations with each other, and are not intended to be limited to the specific combinations disclosed herein. In other words, the structures and functions of the features of one embodiment can be adopted in another embodiment. Also, it is not necessary for all advantages of the invention to be present in a particular embodiment at the same time.

REFERENCES

[Réf. 1] M. van de Weijer et al. "Morbidity of femoropopliteal bypass surgery", *Seminars Vasc. Surg.* 2015; pp. 112-121

[Réf. 2] R. J. Exton et al., "Major groin complications following the use of synthetic grafts", *Eur. J. Vasc. Endovasc. Surg.* 2007; 34, pp. 188-190

[Réf. 3] K. W. H. Chiu et al. "Review of direct anatomical open surgical management of atherosclerotic aorto-iliac occlusive disease", *Eur. J. Vasc. Endovasc. Surg.* 2010; 39, pp. 460-471.

The invention claimed is:

1. A surgical kit for implanting a bypass graft between a first vessel and a second vessel in order to fluidly connect said first and second vessels, the surgical kit comprising: a bypass graft with a first part and a second part, each having a tubular shape, the first part comprising a first lumen and the second part comprising a second lumen, the first and second lumens being adapted to be fluidly connected to form a common lumen when the bypass graft is implanted, wherein:

the first part comprises a first hook portion configured to be deployed and implanted into the first vessel, and a first bypass portion configured to be deployed outside the first vessel;

the second part comprises a second hook portion configured to be deployed and implanted into the second vessel, and a second bypass portion configured to be deployed outside the second vessel and within the first lumen of the first part;

the first bypass portion of the first part is puncturable; and the surgical kit further comprising:

a first retractable outer sheath adapted to contain the first part and retractable over the first part so as to allow the deployment of the first hook portion and first bypass portion, and a second retractable outer sheath adapted to contain the second part and retractable over the second part so as to allow the deployment of the second hook portion and second bypass portion.

2. Surgical kit according to claim 1, wherein the first bypass portion of the first part comprises a region including a flexible material configured to receive a puncture and hermetically accommodate the second retractable outer sheath when the second retractable outer sheath is inserted through the puncture.

3. Surgical kit according to claim 1, wherein the first hook portion, the first bypass portion, the second hook portion and the second bypass portion are radially expandable.

4. Surgical kit according to claim 1, wherein the second retractable outer sheath has an outer diameter of at least 4 mm.

5. A percutaneous bypass method for implanting a bypass graft between a first vessel and a second vessel in order to fluidly connect said first and second vessels, the bypass graft comprising a first part and a second part, each having a tubular shape, the first part comprising a first lumen and the second part comprising a second lumen, the first and second lumens being fluidly connected to form a common lumen when the bypass graft is implanted, wherein the method comprises the following steps:

forming a first aperture in a wall of the first vessel;

partly introducing a first sheath through the first aperture and retracting the first sheath so as to:

deploy and implant a first hook portion of the first part into the first vessel, and deploy a first bypass portion of the first part outside the first vessel;

forming a puncture in the first bypass portion;

passing a guide through the puncture and through the first lumen, towards the second vessel;

forming a second aperture in a wall of the second vessel;

inserting a second sheath, from the outside to the inside of the first bypass portion, through the puncture and through the first lumen; and partly introducing the second sheath through the second aperture and retracting the second sheath so as to:

deploy and implant a second hook portion of the second part into the second vessel, and deploy a second bypass portion of the second part outside the second vessel, from the second vessel to the first part, and within the first lumen.

6. The method according to claim 5, wherein the first hook portion and the first bypass portion are radially expandable and expand radially when retracting the first sheath, and wherein the second hook portion and the second bypass portion are radially expandable and expand radially when retracting the second sheath.

7. The method according to claim 5, wherein the first bypass portion comprises a region including a flexible material configured to maintain the puncture hermetic when inserting the second sheath therethrough.

8. The method according to claim 5, wherein the second sheath has an outer diameter of at least 4 mm.

9. The method according to claim 5, wherein the first vessel is a popliteal artery and/or the second vessel is a femoral artery.

10. The method according to claim 5, wherein a blood flow through the first vessel and/or the second vessel is occluded.

11. The method according to claim 5, wherein at least one step is performed under at least one of duplex scanning control, X-Ray control and fluoroscopic imaging.

12. A method for treating a peripheral vascular disease affecting a patient, comprising the percutaneous bypass method according to claim 5.

13. The method according to claim 5, wherein the first bypass portion of the first part comprises a region including a flexible material configured to hermetically seal the puncture when the bypass graft is implanted.

14. Surgical kit according to claim 1, wherein the first bypass portion of the first part comprises a region including a flexible material configured to receive a puncture and hermetically seal the puncture when the bypass graft is implanted.

* * * * *